United States Patent
Burattin

(10) Patent No.: US 11,020,365 B2
(45) Date of Patent: Jun. 1, 2021

(54) MIXTURE OF FATTY ACIDS FOR USE IN THE TREATMENT OF INFLAMMATORY PATHOLOGIES

(71) Applicant: Again Life Italia SRL, Thiene (IT)

(72) Inventor: Lodovico Burattin, Treviso (IT)

(73) Assignee: AGAIN LIFE ITALIA SRL, Schio (IT)

( * ) Notice: Subject to any disclaimer, the term of this patent is extended or adjusted under 35 U.S.C. 154(b) by 531 days.

(21) Appl. No.: 14/772,768

(22) PCT Filed: Mar. 4, 2014

(86) PCT No.: PCT/EP2014/054163
§ 371 (c)(1),
(2) Date: Sep. 3, 2015

(87) PCT Pub. No.: WO2014/135529
PCT Pub. Date: Sep. 12, 2014

(65) Prior Publication Data
US 2016/0015666 A1    Jan. 21, 2016

Related U.S. Application Data

(60) Provisional application No. 61/774,796, filed on Mar. 8, 2013.

(30) Foreign Application Priority Data

Mar. 8, 2013  (IT) .......................... MI2013A000354

(51) Int. Cl.
| | | |
|---|---|---|
| A61K 31/202 | (2006.01) | |
| A61K 9/08 | (2006.01) | |
| A61K 9/14 | (2006.01) | |
| A61K 31/20 | (2006.01) | |
| A61K 31/201 | (2006.01) | |
| A61K 45/06 | (2006.01) | |

(52) U.S. Cl.
CPC .............. *A61K 31/202* (2013.01); *A61K 9/08* (2013.01); *A61K 9/14* (2013.01); *A61K 31/20* (2013.01); *A61K 31/201* (2013.01); *A61K 45/06* (2013.01)

(58) Field of Classification Search
CPC combination set(s) only.
See application file for complete search history.

(56) References Cited

U.S. PATENT DOCUMENTS

| | | |
|---|---|---|
| 5,925,679 A | 7/1999 | Mather |
| 2005/0208162 A1 | 9/2005 | Spencer |
| 2008/0057552 A1* | 3/2008 | Lee .......................... C11B 3/003 435/134 |
| 2009/0297491 A1* | 12/2009 | Bromley .............. A61K 31/122 424/94.1 |
| 2010/0113387 A1 | 5/2010 | Loftsson |
| 2012/0252888 A1 | 10/2012 | Pantzaris |

FOREIGN PATENT DOCUMENTS

| | | |
|---|---|---|
| DE | WO 2011/027373 | 3/2011 |
| JP | 2009149599 A | 7/2009 |

OTHER PUBLICATIONS

Kuehl et al., The Identification of N-(2-hydroxyethyl)-palmitamide as a naturally occurring anti-inflammatory agent, 1957, J. Am. Chem. Soc., 79(20), pp. 5577-5578 (Year: 1957).*
Fritsche, Adv Nutr, 2015, 5, 293S-301S.
Harvey, et al., Clinical Nutrition, 2010, 29, 492-500.
Hubbard, et al., Journal of Nutrition, 1996, 126, 1563-1570.
Lee, et al., Journal of Biological Chemistry. 2001, 276, 16683-16689.

* cited by examiner

*Primary Examiner* — Kortney L. Klinkel
*Assistant Examiner* — Tori Strong
(74) *Attorney, Agent, or Firm* — Hueschen and Sage

(57) ABSTRACT

This invention relates to a mixture of at least three fatty acids selected from palmitic acid, oleic acid, stearic acid, linoleic acid, alpha-linolenic acid, gamma-linolenic acid, eicosapentaenoic acid (EPA), docosahexaenoic acid (DHA), azelaic acid and myristic acid. This invention also relates to the use of the aforesaid mixture in the treatment of inflammatory pathologies.

34 Claims, 7 Drawing Sheets

FIGURE 1:

| Chemical name | Chemical structure |
|---|---|
| Palmitic acid | 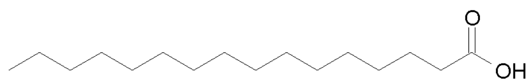 |
| Oleic acid | 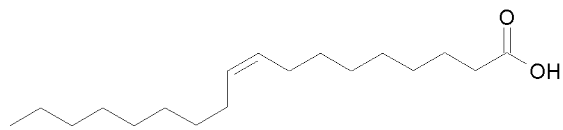 |
| Stearic acid | 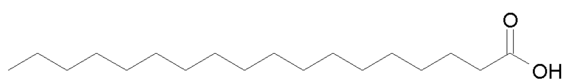 |
| Linoleic acid | 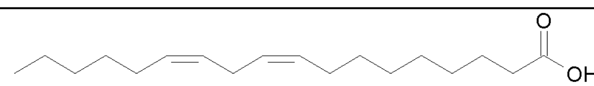 |
| Alpha linolenic acid | 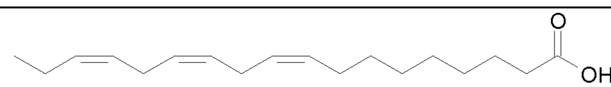 |
| Gamma linolenic acid | 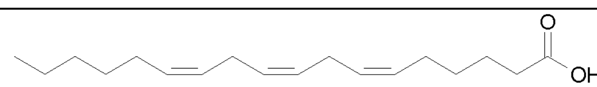 |
| Eicosapentaenoic acid | 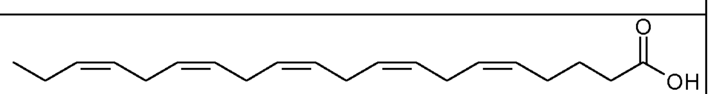 |
| Docosaesaenoic acid | 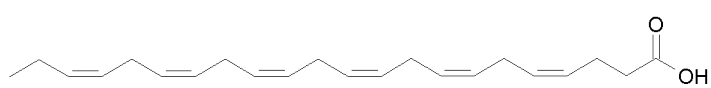 |
| Azelaic acid | 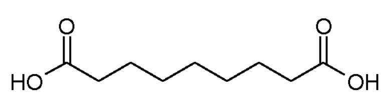 |
| Myristic acid | 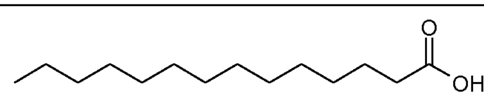 |

MIXTURE OF FATTY ACIDS FOR USE IN THE TREATMENT OF INFLAMMATORY PATHOLOGIES

STATE OF THE ART

Fatty acids are aliphatic carboxylic acids and they represent the constituent ingredients of almost all complex lipids and of vegetable and animal fats. These compounds can be classified according to the length of the carbon chain and/or the presence of double bonds within the said chain (saturated, unsaturated fatty acids).

In particular, some unsaturated fatty acids are considered to be essential because they are not synthesised by the body, instead they must be supplemented by diet. Among these, some acids are distinguished according to the position of the last double bond in the carbon chain, such as omega-3, wherein the last double bond is found on the third carbon from the end (for example linolenic acid), omega-6 wherein the last double bond is found on the sixth carbon from the end (for example linoleic acid) or, furthermore, omega-9 wherein the last double bond is found on the ninth carbon from the end (e.g. oleic acid).

In 1964, Bergstrom, Samuelsson et al. (Nutrition classics. Biochimica et Biophysica Acta 90:207-10, 1964. The enzymatic formation of prostaglandin E2 from arachidonic acid. Prostaglandins and related factors 32) demonstrated the role and the biological effects of lipids in the inflammatory process and in other diseases.

In 1979, the first phospholipid was discovered, namely phosphatidylinositol, along with the role thereof in the activation of cellular response processes, the said phospholipid being able to activate and control reactivity through messaging elements.

Lipids, therefore, play different roles in the body, including acting as chemical messengers which can cause changes in the role of an individual cell or determine actions which can change the microenvironment, as in the case of the processes involved in the response to inflammatory insults. Lipids in esterified form can fit into the membrane and be transported as signal elements for other cells. These compounds can also bind to certain proteins and remain inactive until they reach the site of action and bind to the appropriate receptor.

Essential fatty acids, such as linoleic acid and linolenic acid, are known to be precursors of the arachidonic acid present on membrane phospholipids (e.g. those of the cell membrane) and of many different types of eicosanoids, i.e. substances involved in the body's inflammatory response, including hydroxyeicosatetraenoic acids, prostanoids (prostaglandins, thromboxanes, and prostacyclins), leukotrienes, lipoxins and resolvins, chemical mediators which play an important role in pain, fever, oedema, blood coagulation and, more in general, inflammation.

As is known, the inflammatory response is a multifactorial physiological reaction characterised by the participation of different cells from the immune system, e.g. mast cells, macrophages, basophils and/or lymphocytes, with different intervention times.

One of the first cells to intervene in the inflammatory process is the mast cell, whose capacity to respond and trigger the inflammatory process is in the order of microseconds.

The activation thereof generates a series of reactions resulting in the release of preformed mediators contained within the cytoplasm thereof; in rapid succession, the macrophages are recalled and activated.

The function of macrophages is structured into two phases: the first, known as M1, involves the activation of a series of reactions resulting in the release into the microenvironment of chemical mediators, such as NGF (Nerve Growth Factor), VEGF (Vascular Endothelial Growth Factor), FGF (Fibroblast Growth Factor), histamine, interleukins, cytokines, and lipid products, such as arachidonic acid, prostaglandins and heparin, which can trigger and support the inflammatory process as well as to "attract" the other cells in the immune system to the site of inflammation. The second phase, known as M2, involves the activation of the 'scavenger' phenomenon aimed at eliminating the waste resulting from the destruction of the agent responsible for the inflammatory action. Between the macrophage activation phase in M1 and M2, the basophils—whose role is to release histamine into the microenvironment subjected to the aggression of the inflammatory agent—are attracted and activated, leading to vasodilation and, consequently, oedema as a result of immune cell diapedesis or extravasation.

When the inflammatory reaction has reached the diapedesis phase, the lymphocytes—whose role is to counteract the pathogenic agent—reach the area. The entire inflammatory process is triggered in just a few seconds.

All complex biological systems are regulated by a system of opposition based on agonism and antagonism mechanisms. More generally, the degranulation of the mast cell mediators triggers a series of phenomena which are synthesised during the inflammatory process.

The aforesaid cells in the immune system are self-regulated by means of fine receptor mechanisms involving a sophisticated system of receptors, expressed in the cytoplasmic membrane, which can be overexpressed during stimulation processes.

This overexpression determines a release, within the extra-cellular space, of a series of chemical mediators, which trigger a series of events whose purpose is to defend the tissue microenvironment and bring about repair phenomena. The system is regulated by the production of receptor antagonists, which are produced by the cell itself, from fatty acids taken from the cell membrane.

These biological systems are based on receptor control: following stimulation of the pathogenic agent, the cells express specific receptors which are saturated with self-produced mediators, i.e. formed from the fatty acids constituting the membranes of the said cells. The expression of receptors is the means by which the cells involved in the inflammatory process are able to transfer growth factors, interleukins, cytokines, etc., into the microenvironment. The saturation of these receptors allows first the reduction and then the modulation of the degranulation of the mediators present within the cytoplasm of the cells involved in the inflammatory process (the mast cells in particular) until the stimulation induced by the presence of the pathogenic agent is halted.

This regulation means, however, comes to an end when the continuous dwindling of the fatty acids in the cell membranes causes suffering to the cell itself. In this condition, the receptors are overexpressed and, for the cell, this constitutes a degranulation signal aimed at the mediators that trigger defence phenomena which are no longer necessary.

Therefore, if there were no receptor control receptor, the cells would obviously induce the degranulation of everything present in the cytoplasm, leading to the attraction of other cells to the microenvironment. This would then lead to an irritation of the system, which—remaining active—could become a source of damage, giving rise to chronic inflammatory pathologies and autoimmune diseases, such as rheumatoid arthritis, multiple sclerosis, and systemic lupus erythematosus.

It is therefore very important that, in these pathological conditions, the body can control the overactive inflammatory process through the formation of a receptor antagonist consisting of fatty acids taken from the membrane of the same cells.

At present, to meet this need, research has concentrated on dietary strategies designed to reduce the synthesis of pro-inflammatory chemical mediators, such as prostaglandins, by reducing the consumption of vegetable oils and fatty meats, and increasing the intake of fish and certain particular oils, such as flax and hemp. With this method, it is thought that greater amounts of eicosapentaenoic acid and docosahexaenoic acid (omega-3) would be incorporated into the membrane phospholipids instead of arachidonic acid.

Nevertheless, it is well known that these dietary strategies are not sufficient to eradicate major inflammatory pathologies such as rheumatoid arthritis, chronic ulcerative colitis, systemic lupus erythematosus, pelvic inflammatory disease, or atherosclerosis, and recourse to pharmacological therapies is necessary.

At present, the pharmacological therapies used for inflammatory pathologies include corticosteroids (such as cortisone and analogue substances) or NSAIDs (non-steroidal anti-inflammatory drugs), which act on different levels of the arachidonic acid cascade. Corticosteroids counteract the release of arachidonic acid from phospholipids through the inhibition of the phospholipase activity, including phospholipase A2 (PLA2) and phospholipase C (PLC). In particular, the mechanism by which corticosteroids exert their anti-inflammatory and immunosuppressive action is highly structured and involves several biochemical processes implemented by cell in response to potentially harmful stimuli (e.g. infectious agents, allergens, foreign substances, abnormal cells, etc.).

The role of this mechanism is to trigger an immune response, maintain it until the risk is eliminated and then deaden the response so that it does not go on to become harmful (as happens, for example, in chronic inflammation cases or autoimmune diseases). In particular, the corticosteroids inhibit the cellular processes that lead to the synthesis of pro-inflammatory and immunostimulatory substances and, vice versa, activate the cellular processes that lead to the synthesis of anti-inflammatory and immunosuppressive substances, in order to reduce the symptoms of the disease.

Apart from the anti-inflammatory/immunosuppressive effect, the side effects of the synthesised corticosteroids generally stem from the fact that they interfere with the body's homeostatic systems and therefore may cause: hypertension, water retention, hyperglycemia, potassium loss, osteoporosis, muscle hypertrophy, capillary fragility, delayed wound healing, hyperlipidaemia, accumulation of adipose tissue in the face, neck and abdomen, gastroduodenal ulcers, increased blood coagulability, haematological disorders, euphoria, and insomnia.

In prolonged treatment, moreover, these pharmacological substances tend to inhibit the production of analogue natural hormones by the adrenal glands, thereby causing a situation of adrenal insufficiency, which occurs with serious consequences, especially upon discontinuation of the therapy. Furthermore, prolonged use of corticosteroids is linked to the immunosuppressive action thereof, which increases susceptibility to infections.

NSAIDs, meanwhile, interfere with the arachidonic acid cascade on a different level, by inhibiting cyclooxygenases COX1 and 2, which are involved in inflammatory processes. The most common side effects are those affecting the digestive system, in particular, the stomach, and include pain, burning sensations, or nausea, and ulceration of the gastric mucosa with possible bleeding; as well as skin reactions in susceptible individuals (erythema, urticaria).

Therefore, there is a need to identify one or more compounds for the treatment of inflammation which can effectively block the hyperactivity of the inflammatory process, reducing the side effects associated with conventional treatments.

BRIEF DESCRIPTION OF THE FIGURES

FIG. 1: Summary table containing the chemical structures of the fatty acids of the present invention.

DESCRIPTION

Figure 2:
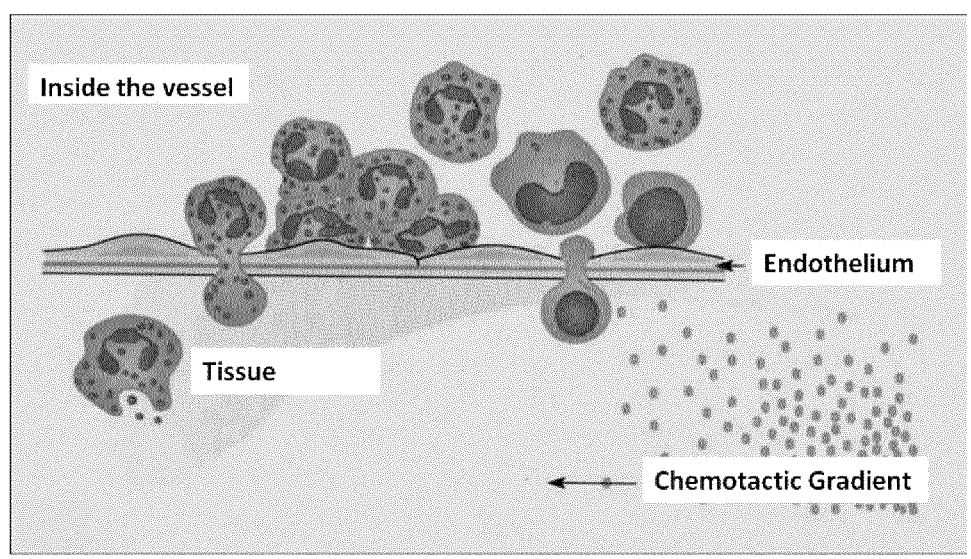
FIG. 2: Mechanism of action of macrophages

Surprisingly, it has been found that a mixture of specific fatty acids can efficiently treat the inflammatory process, with improved control of the regulatory system and without side effects, by means of the biological modulation of the cells involved in the inflammatory process (BMIC Biological Modulation of Inflammatory Cells).

One object of the present invention is, therefore, a mixture of at least three fatty acids, containing from 8 to 24 carbon atoms, said fatty acids can be either saturated, unsaturated, or mixtures thereof.

The mixture of the present invention preferably contains from three to ten fatty acids, and, more preferably, said mixture contains four, five, eight or nine fatty acids.

Said fatty acids are preferably selected from palmitic acid, oleic acid, stearic acid, linoleic acid, alpha-linolenic acid, gamma-linolenic acid, eicosapentaenoic acid (EPA), docosahexaenoic acid (DHA), azelaic acid and myristic acid, or a mixture thereof.

The term "palmitic acid", according to this invention, refers to hexadecanoic acid, i.e. a saturated monocarboxylic acid containing 16 carbon atoms (FIG. 1).

The term "oleic acid", according to this invention, refers to cis-9-octadecenoic acid, i.e. an unsaturated monocarboxylic acid (omega-9) containing 18 carbon atoms (FIG. 1).

The term "stearic acid", according to this invention, refers to octadecanoic acid, i.e. a saturated monocarboxylic acid containing 18 carbon atoms (FIG. 1).

The term "linoleic acid", according to this invention, refers to cis,cis-9,12-octadecenoic acid, i.e. an unsaturated monocarboxylic acid (omega-6) containing 18 carbon atoms (FIG. 1).

The term "alpha-linolenic acid", according to this invention, refers to cis,cis,cis-9,12,15-octadecatrienoic acid, i.e. an unsaturated monocarboxylic acid (omega-3) containing 18 carbon atoms (FIG. 1).

The term "gamma-linolenic acid", according to this invention, refers to cis,cis,cis-6,9,12-octadecatrienoic acid, i.e. an unsaturated monocarboxylic acid (omega-6) containing 18 carbon atoms (FIG. 1).

The term "eicosapentaenoic acid (EPA)", according to this invention, refers to (5Z,8Z,11 Z,14Z,17Z)-Eicosa-5,8,11,14,17-pentenoic acid, i.e. to an unsaturated monocarboxylic acid (omega-3) containing 20 carbon atoms (FIG. 1).

The term "docosahexaenoic acid (DHA)", according to this invention, refers to (4Z,7Z,10Z,13Z,16Z,19Z)-docosa-4,7,10,13,16,19-hexaenoic acid, i.e. to an unsaturated monocarboxylic acid (omega-3) containing 22 carbon atoms (FIG. 1).

The term "azelaic acid", according to this invention, refers to nonanedioic acid, i.e. a saturated dicarboxylic acid containing 9 carbon atoms (FIG. 1).

The term "myristic acid", according to this invention, refers to tetradecanoic acid, i.e. a saturated monocarboxylic acid containing 14 carbon atoms (FIG. 1).

Preferably, the mixture of the present invention contains six fatty acids, namely: palmitic acid, oleic acid, linoleic acid, alpha-linolenic acid, gamma-linolenic acid, and eicosapentaenoic acid (EPA).

Preferably, the mixture of the present invention contains seven fatty acids, namely: palmitic acid, oleic acid, stearic acid, linoleic acid, alpha-linolenic acid, and eicosapentaenoic acid (EPA) and docosahexaenoic acid (DHA).

More preferably, the mixture of the present invention contains four fatty acids, namely: palmitic acid, oleic acid, stearic acid, and linoleic acid.

More preferably, the mixture of the present invention contains five fatty acids, namely: palmitic acid, oleic acid, stearic acid, linoleic acid, and alpha-linolenic acid.

More preferably, said mixture contains eight fatty acids, namely: palmitic acid, oleic acid, stearic acid, linoleic acid, alpha-linolenic acid, gamma-linolenic acid, eicosapentaenoic acid (EPA) and docosahexaenoic acid (DHA).

More preferably, said mixture contains nine fatty acids, namely: palmitic acid, oleic acid, stearic acid, linoleic acid, alpha-linolenic acid, gamma-linolenic acid, eicosapentaenoic acid (EPA), docosahexaenoic acid (DHA) and azelaic acid.

According to one embodiment of the present invention, the palmitic acid is contained in the mixture in a quantity comprised between 0.2% and 48% by weight; the oleic acid is contained in the mixture in a quantity comprised between 0.2% and 38% by weight; the stearic acid is contained in the mixture in a quantity comprised between 0.2% and 42% by weight; the linoleic acid is contained in the mixture in a quantity comprised between 0.2% and 40% by weight; the alpha-linolenic acid is contained in the mixture in a quantity comprised between 0.2% and 38% by weight; the gamma-linoleic acid is contained in the mixture in a quantity comprised between 0.2% and 30% by weight; the eicosapentaenoic acid is contained in the mixture in a quantity comprised between 0.2% and 25% by weight; the docosahexaenoic acid is contained in the mixture in a quantity comprised between 0.2% and 25% by weight; the azelaic acid is contained in the mixture in a quantity comprised between 0.2% and 40% by weight; the myristic acid is contained in the mixture in a quantity comprised between 0.005% and 0.01% by weight; The aforesaid percentages are quantities by weight expressed with respect to the total weight of the mixture.

When the aforesaid mixture of the present invention contains four fatty acids, the palmitic acid is contained in the aforesaid mixture in a quantity comprised between 0.2% and 48% by weight, preferably between 30% and 45% by weight, and more preferably to about 40% of the total weight of the mixture.

In the aforesaid mixture, the oleic acid is contained in a quantity comprised between 0.2% and 38% by weight, preferably between 15% and 30%, by weight, and more preferably to about 25% of the total weight of the mixture.

In the aforesaid mixture, the stearic acid is contained in a quantity comprised between 0.2% and 42% by weight, preferably between 20% and 35% by weight, and more preferably to about 32% of the total weight of the mixture.

In the aforesaid mixture, the linoleic acid is contained in a quantity comprised between 0.2% and 38% by weight, preferably between 1% and 4% by weight, and more preferably to about 3% of the total weight of the mixture.

When the aforesaid mixture of the present invention contains five fatty acids, the palmitic acid is contained in the aforesaid mixture in a quantity comprised between 0.2% and 48% by weight, preferably between 20% and 40% by weight, and more preferably to about 38% of the total weight of the mixture.

In the aforesaid mixture, the oleic acid is contained in a quantity comprised between 0.2% and 38% by weight, preferably between 20% and 30% by weight, and more preferably to about 27% of the total weight of the mixture.

In the aforesaid mixture, the stearic acid is contained in a quantity comprised between 0.2% and 42% by weight, preferably between 7% and 15% by weight, and more preferably to about 10% of the total weight of the mixture.

In the aforesaid mixture, the linoleic acid is contained in a quantity comprised between 0.2% and 40% by weight, preferably between 8% and 20% by weight, and more preferably to about 15% of the total weight of the mixture.

In the aforesaid mixture, the alpha-linolenic acid is contained in a quantity comprised between 0.2% and 38% by weight, preferably between 2% and 15% by weight, and more preferably to about 10% of the total weight of the mixture.

When the aforesaid mixture of the present invention contains eight fatty acids, the palmitic acid is contained in the aforesaid mixture in a quantity comprised between 0.2% and 48% by weight, preferably between 20% and 38% by weight, and more preferably to about 30% of the total weight of the mixture.

In the aforesaid mixture, the oleic acid is contained in a quantity comprised between 0.2% and 38% by weight, preferably between 10% and 15% by weight, and more preferably to about 12% of the total weight of the mixture.

In the aforesaid mixture, the stearic acid is contained in a quantity comprised between 0.2% and 42% by weight, preferably between 8% and 15% by weight, and more preferably to about 12% of the total weight of the mixture.

In the aforesaid mixture, the linoleic acid is contained in a quantity comprised between 0.2% and 40% by weight, preferably between 10% and 20% by weight, and more preferably to about 18% of the total weight of the mixture.

In the aforesaid mixture, the alpha-linolenic acid is contained in a quantity comprised between 0.2% and 38% by weight, preferably between 10% and 15% by weight, and more preferably to about 12% of the total weight of the mixture.

In the aforesaid mixture, the gamma-linoleic acid is contained in a quantity comprised between 0.2% and 3% by weight, preferably between 1% and 3% by weight, and more preferably to about 2% of the total weight of the mixture.

In the aforesaid mixture, the eicosapentaenoic acid is contained in a quantity comprised between 0.2% and 25% by weight, preferably between 5% and 10% by weight, and more preferably to about 8% of the total weight of the mixture.

In the aforesaid mixture, the docosahexaenoic acid is contained in a quantity comprised between 0.2% and 25% by weight, preferably between 4% and 10% by weight, and more preferably to about 6% of the total weight of the mixture.

When the aforesaid mixture of the present invention contains nine fatty acids, the palmitic acid is contained in the aforesaid mixture in a quantity comprised between 0.2% and 48% by weight, preferably between 20% and 30% by weight, and more preferably to about 25% of the total weight of the mixture.

In the aforesaid mixture, the oleic acid is contained in a quantity comprised between 0.2% and 38% by weight, preferably between 10% and 16% by weight, and more preferably to about 14% of the total weight of the mixture.

In the aforesaid mixture, the stearic acid is contained in a quantity comprised between 0.2% and 42% by weight, preferably between 8% and 15% by weight, and more preferably to about 12% of the total weight of the mixture.

In the aforesaid mixture, the linoleic acid is contained in a quantity comprised between 0.2% and 40% by weight, preferably between 15% and 25% by weight, and more preferably to about 20% of the total weight of the mixture.

In the aforesaid mixture, the alpha-linolenic acid is contained in a quantity comprised between 0.2% and 38% by weight, preferably between 5% and 10% by weight, and more preferably to about 8% of the total weight of the mixture.

In the aforesaid mixture, the gamma-linoleic acid is contained in a quantity comprised between 0.2% and 30% by weight, preferably between 2% and 6% by weight, and more preferably to about 4% of the total weight of the mixture.

In the aforesaid mixture, the eicosapentaenoic acid is contained in a quantity comprised between 0.2% and 25% by weight, preferably between 5% and 10% by weight, and more preferably to about 7% of the total weight of the mixture.

In the aforesaid mixture, the docosahexaenoic acid is contained in a quantity comprised between 0.2% and 25% by weight, preferably between 5% and 10% by weight, and more preferably to about 8% of the total weight of the mixture.

In the aforesaid mixture, the azelaic acid is contained in a quantity comprised between 0.2% and 40% by weight, preferably between 1% and 3% by weight, and more preferably to about 2% of the total weight of the mixture.

According to a preferred embodiment of this invention, when the mixture contains four fatty acids, such as palmitic acid, oleic acid, stearic acid, and linoleic acid, they are present in a weight ratio of about 1.6:1:1.28.0.12, respectively.

According to a preferred embodiment of this invention, when the mixture contains five fatty acids, such as palmitic acid, oleic acid, stearic acid, linoleic acid, and alpha-linolenic acid, they are present in a weight ratio of about 1.9:1.35:0.5:0.75:0.5, respectively.

According to a preferred embodiment of this invention, when the mixture according to this invention contains eight fatty acids, such as palmitic acid, oleic acid, stearic acid, linoleic acid, alpha-linolenic acid, gamma-linolenic acid, eicosapentaenoic acid, and docosahexaenoic acid, they are present in a weight ratio of about 2.4:0.96:0.96:1.44:0.96:0.16:0.64:0.48 respectively.

According to a further preferred embodiment of this invention, when the mixture according to this invention contains nine fatty acids, such as palmitic acid, oleic acid, stearic acid, linoleic acid, alpha-linolenic acid, gamma-linolenic acid, eicosapentaenoic acid, docosahexaenoic acid and azelaic acid, they are preferably present in a weight ratio of about 2.25:1.26:1.08:1.80:0.72:0.36:0.63:0.72:0.18 respectively.

Surprisingly, it has been noted that by establishing a pool of the aforesaid fatty acids, in particular of four, five, eight, or nine fatty acids according to this invention, it has been possible to establish control of the cells involved in inflammatory processes, such as mast cells, macrophages, basophils, and lymphocytes.

This system of administration of the fatty acids has two important advantages:
1) a more rapid and reactive response to the hyperstimulation induced by the inflammatory agent: the membrane lipids in the cell do not dwindle, thereby resulting in temporal dispersion;
2) significant energy savings: the cell does not have to use energy to recover lipids from the membranes and then replace them.

Indeed, it has been observed that, by providing the pool of fatty acids according to this invention, improved control of the inflammatory process is obtained and physiological conditions and normal conditions of the microenvironment involved are restored in shorter times, all with respect to the prior art.

A further object of the present invention is a pharmaceutical, cosmetic, and/or dietary composition comprising the above mixture and at least one physiologically acceptable excipient.

A physiologically acceptable excipient according to this invention is any excipient known by a person skilled in the art to be useful in the preparation of pharmaceutical and/or cosmetic compositions.

The other excipients are usually classified according to the function they perform in the final composition. Preferable suitable excipients according to this invention include, for example, diluents, absorbents, glidants, binders, lubricants, surfactants, disintegrants, preservatives, antioxidants, or mixtures thereof.

Alternatively, the excipients may be classified according to the functional group present in their chemical structure, such as sugars, amides, ethers, alcohols and suchlike.

A particularly preferred excipient according to the present invention is N-2-hydroxyethyl palmitamide.

According to one embodiment of this invention, the aforesaid composition comprises a mixture of at least three fatty acids selected from the following: palmitic acid, oleic acid, stearic acid, linoleic acid, alpha-linolenic acid, gamma-linolenic acid, eicosapentaenoic acid (EPA), docosahexaenoic acid (DHA), azelaic acid and myristic acid, an at least one pharmaceutically acceptable excipient.

Preferably, said composition comprises a mixture containing between three and ten fatty acids, and at least one pharmaceutically acceptable excipient.

According to one embodiment of this invention, the palmitic acid is contained in the composition in a quantity comprised between 5% and 45% by weight; the oleic acid is contained in the composition in a quantity comprised between 2% and 35% by weight; the stearic acid is contained in the composition in a quantity comprised between 2% and 35% by weight; the linoleic acid is contained in the composition in a quantity comprised between 1% and 40% by weight; the alpha-linolenic acid is contained in the composition in a quantity comprised between 1% and 25% by weight; the gamma-linolenic acid is contained in the composition in a quantity comprised between 0.5% and 10% by weight; the eicosapentaenoic acid is contained in the composition in a quantity comprised between 1% and 20% by weight; the docosahexaenoic acid is contained in the composition in a quantity comprised between 1% and 25% by weight; the azelaic acid is contained in the composition in a quantity comprised between 0.5% and 10% by weight; the myristic acid is contained in the composition in a quantity comprised between 0.05% and 1% by weight;

The aforesaid percentages are quantities by weight expressed with respect to the total weight of the composition.

According to a preferred embodiment of this invention, said composition contains a mixture comprising four fatty acids and at least one pharmaceutically acceptable excipient.

When the mixture of the present invention comprises four fatty acids, the palmitic acid is contained in the composition in a quantity comprised between 2% and 40% by weight, preferably between 5% and 25% by weight, and more preferably to about 6% of the total weight of the composition.

In the aforesaid composition, the oleic acid is contained in a quantity comprised between 1% and 35% by weight, preferably between 2% and 10% by weight, and more preferably to about 4% of the total weight of the composition.

In the aforesaid composition, the stearic acid is contained in a quantity comprised between 0.5% and 15% by weight, preferably between 2% and 10% by weight, and more preferably to about 5% of the total weight of the composition.

In the aforesaid composition, the linoleic acid is contained in a quantity comprised between 0.5% and 5% by weight, preferably between 1% and 3% by weight, and more preferably to about 1% of the total weight of the composition.

According to a preferred embodiment of this invention, said composition contains a mixture comprising five fatty acids and at least one pharmaceutically acceptable excipient.

When the mixture of the present invention comprises five fatty acids, the palmitic acid is contained in the composition in a quantity comprised between 1% and 20% by weight, preferably between 3% and 10% by weight, and more preferably to about 6% of the total weight of the composition.

In the aforesaid composition, the oleic acid is contained in a quantity comprised between 1% and 15% by weight, preferably between 2% and 8% by weight, and more preferably to about 4.5% of the total weight of the composition.

In the aforesaid composition, the stearic acid is contained in a quantity comprised between 0.5% and 7%, preferably between 1% and 5% by weight, and more preferably to about 2% of the total weight of the composition.

In the aforesaid composition, the linoleic acid is contained in a quantity comprised between 0.5% and 10% by weight, preferably between 1% and 5% by weight, and more preferably to about 2.5% of the total weight of the composition.

In the aforesaid composition, the alpha-linolenic acid is contained in a quantity comprised between 0.5% and 10% by weight, preferably between 1% and 6% by weight, and more preferably to about 2% of the total weight of the composition.

According to a preferred embodiment of this invention, said composition contains a mixture comprising eight fatty acids and at least one pharmaceutically acceptable excipient.

When the mixture of the present invention comprises eight fatty acids, the palmitic acid is contained in the composition in a quantity comprised between 1% and 30% by weight, preferably between 3% and 10% by weight, and more preferably to about 6% of the total weight of the composition.

In the aforesaid composition, the oleic acid is contained in a quantity comprised between 1% and 25% by weight, preferably between 5% and 15% by weight, and more preferably to about 10% of the total weight of the composition.

In the aforesaid composition, the stearic acid is contained in a quantity comprised between 1% and 25% by weight, preferably between 5% and 15% by weight, and more preferably to about 10% of the total weight of the composition.

In the aforesaid composition, the linoleic acid is contained in a quantity comprised between 0.2% and 10% by weight, preferably between 0.7% and 5% by weight, and more preferably to about 1% of the total weight of the composition.

In the aforesaid composition, the alpha-linolenic acid is contained in a quantity comprised between 0.2% and 6% by weight, preferably between 0.5% and 4% by weight, and more preferably to about 1% of the total weight of the composition.

In the aforesaid composition, the gamma-linolenic acid is contained in a quantity comprised between 0.04% and 3% by weight, preferably between 0.2% and 1% by weight, and more preferably to about 0.5% of the total weight of the composition.

In the aforesaid composition, the eicosapentaenoic acid is contained in a quantity comprised between 1% and 15% by weight, preferably between 2% and 6% by weight, and more preferably to about 3% of the total weight of the composition.

In the aforesaid composition, the docosahexaenoic acid is contained in a quantity comprised between 0.5% and 7% by weight, preferably between 1% and 4% by weight, and more preferably to about 2% of the total weight of the composition.

In a further preferred embodiment of this invention, said composition contains a mixture comprising nine fatty acids and at least one pharmaceutically acceptable excipient.

When the mixture of the present invention comprises nine fatty acids, the palmitic acid is contained in the composition in a quantity comprised between 1% and 30% by weight, preferably between 3% and 10% by weight, and more preferably to about 7% of the total weight of the composition.

In the aforesaid composition, the oleic acid is contained in a quantity comprised between 1% and 25% by weight, preferably between 5% and 15% by weight, and more preferably to about 10% of the total weight of the composition.

In the aforesaid composition, the stearic acid is contained in a quantity comprised between 1% and 25% by weight, preferably between 5% and 15% by weight, and more preferably to about 10% of the total weight of the composition.

In the aforesaid composition, the linoleic acid is contained in a quantity comprised between 0.2% and 6% by weight, preferably between 0.5% and 3% by weight, and more preferably to about 1% of the total weight of the composition.

In the aforesaid composition, the alpha-linolenic acid is contained in a quantity comprised between 0.2% and 6% by weight, preferably between 0.5% and 4% by weight, and more preferably to about 1% of the total weight of the composition.

In the aforesaid composition, the gamma-linolenic acid is contained in a quantity comprised between 0.04% and 3% by weight, preferably between 0.2% and 1% by weight, and more preferably to about 0.5% of the total weight of the composition.

In the aforesaid composition, the eicosapentaenoic acid is contained in a quantity comprised between 1% and 15% by weight, preferably between 2% and 6% by weight, and more preferably to about 3% of the total weight of the composition.

In the aforesaid composition, the docosahexaenoic acid is contained in a quantity comprised between 0.5% and 7% by weight, preferably between 1% and 4% by weight, and more preferably to about 2% of the total weight of the composition.

In the aforesaid composition, the azelaic acid is contained in a quantity comprised between 0.05% and 2% by weight, preferably between 0.2% and 1% by weight, and more preferably to about 0.5% of the total weight of the composition.

The composition of this invention can be formulated in a form suitable for oral, topical, rectal, vaginal, ophthalmic, or parenteral administration.

In a preferred embodiment of this invention, said oral form can be selected from tablets, capsules, granules, oily capsules, solutions, suspensions, carriers, or nebuliser solutions, and more preferably is selected from capsules, tablets or solutions.

The capsule may be a soft gelatine capsule, a hard capsule, or a capsule containing granules.

According to a further preferred embodiment of this invention, said topical form can be selected from cream, ointment, gel, solution, suspension, spray, patch, or lyophilised granular powder, more preferably is selected from cream, gel, spray, ointment and lyophilised granular powder.

According to a further preferred embodiment of this invention, said form suitable for vaginal administration is a pessary, a catheter, a gel or a solution for endocavitary use.

According to a further preferred embodiment of this invention, said form suitable for rectal administration is a suppository, an enema, or a solution for endocavitary use.

According to a further preferred embodiment of this invention, said form suitable for ophthalmic administration is eye drops, a wash, a cream, or a ointment.

The term "wash" is understood as an eyewash solution.

According to another preferred embodiment of this invention, said form suitable for parenteral administration can be either an aqueous buffer solution or an oily suspension, and preferably said parenteral form is an oily suspension.

According to a further preferred embodiment of this invention, the aforesaid composition is a dermocosmetic composition, a pharmaceutical substance, a dietary supplement, or a drug.

The mixture of fatty acids in the present invention is preferably contained in the aforesaid formulations in a quantity which varies from 10% to 60% by weight, and preferably from 15% to 45% of the total weight of the formulation.

According to one embodiment of this invention, the composition of the present invention containing a mixture of four fatty acids is preferably formulated in a topical form.

According to one embodiment of this invention, the composition of the present invention containing a mixture of five fatty acids is preferably formulated in a topical form or an oral form.

According to one embodiment of this invention, the composition of the present invention containing a mixture of eight fatty acids is preferably formulated in an oral form, and more preferably in a tablet form or a suspension form.

Said composition containing a mixture of eight fatty acids is preferably formulated in a parenteral form or in a rectal form.

According to further embodiment of this invention, the composition of the invention containing a mixture of nine fatty acids is formulated in an oral form, more preferably in a tablet form or suspension form, or in a topical form, and more preferably in a cream form, gel form, or ointment form.

In the aforesaid oral form containing said mixture of nine fatty acids, the azelaic acid is contained in a quantity comprised between 0.04% and 0.5% by weight, preferably between 0.08% and 0.4% by weight, and more preferably to about 0.2%.

In the aforesaid topical form containing said mixture of nine fatty acids, the azelaic acid is contained in a quantity comprised between 0.05% and 2% by weight, preferably between 0.2% and 1% by weight, and more preferably to about 0.5%.

According to the invention, the composition of the present invention may be administered to humans, intended to comprise both adults and the "paediatric population" (where the term "paediatric population" is understood as the part of the population ranging from birth to eighteen years of age), and to animals.

A further object of the present invention is a mixture containing at least three fatty acids, preferably between three and ten fatty acids, and more preferably four, five, eight, or nine fatty acids and/or a composition containing said mixture, for use in the treatment of inflammatory pathologies.

The aforesaid inflammatory pathologies are of the acute or chronic variety and include: dermatological pathologies, such as atopic dermatitis, dermatomyositis, scleroderma, psoriasis, polymyositis, pemphigus, pemphigoid epidermolysis bullosa; ophthalmic pathologies, such as Sjogren's syndrome, sympathetic ophthalmia, uveitis, and uveo-retinitis; mucosal pathologies, such as inflammation of the gastrointestinal mucous membranes (Crohn's disease) and inflammation of the oral and genital mucosa; articular and connective pathologies, such as rheumatoid arthritis, psoriatic arthritis, arthritis from lupus erythematosus, and discoid and systemic lupus erythematosus; chronic pathological inflammations, such as chronic solar dermatitis, asthma and intestinal and pulmonary fibrosis, and chronic arthritis, degenerative pathologies affecting the peripheral nervous system (PNS) and central nervous system (CNS), such as multiple sclerosis, autoimmune neurodegenerative pathologies, non-autoimmune neurodegenerative pathologies, inflammatory processes connected to the CNS, such as Parkinson's disease, senile dementia, bacterial meningitis, HIV infection and traumatic injuries, and pathologies of the PNS, such as radiculopathy caused by inflammation; pathologies of the central and peripheral nervous system where the inflammatory processes follow the first ischemic insult, such as neuropathies due to compression, as well as traumatic neuropathies, cerebral strokes and cranial traumas; cardiological diseases deriving from perfusion phenomena as a consequence of ischemic injuries; inflammatory pathologies associated with fibrosis, such as allergic conjunctivitis, giant papillary conjunctivitis, dietary allergies, abnormal cicatrisation, such as hypertrophic cicatrix, keloids and ocular cicatricial pemphigoid; pathologies in which renal function is altered as a result of inflammation of the kidneys.

As regards administration to animals of the composition of the present invention, the local and/or systemic anti-inflammatory action exerted by the pool of fatty acids is useful in the treatment of neurogenic inflammation (e.g. spinal cord compression, nerve lesions in dogs), articular and connective pathologies such as laminitis in horses (where the use of cortisone drugs is not possible), arthritis, respiratory pathologies, ophthalmic inflammation, keratoconjunctivitis sicca, and allergic inflammatory manifestations, including food allergies.

The composition of this invention is preferably administered daily, to both humans and animals, within a range of one to four doses a day.

Said dose preferably contains from 0.1 to 50 mg of composition/kg of the patient's bodyweight, and more preferably from 0.5 to 20 mg/kg of the patient's bodyweight. According to a preferred embodiment of the present invention, said composition is administered for at least four weeks.

EXPERIMENTAL PART

EXAMPLES

The following mixtures according to the present invention were prepared.

Example 1

Eicosapentaenoic acid (EPA) ranging from 0.5% to 15%
Docosahexaenoic acid (DHA) ranging from 0.5% to 15%
Palmitic acid ranging from 0.5% to 35%
Oleic acid ranging from 0.5% to 35%
Stearic acid ranging from 0.5% to 15%
Gamma-linolenic acid ranging from 0.5% to 15%
Alpha-linolenic acid ranging from 0.5% to 15%
Azelaic acid ranging from 0.5% to 35%
Linoleic acid ranging from 0.5% to 35%

Example 2

Eicosapentaenoic acid (EPA) ranging from 3% to 10%
Docosahexaenoic acid (DHA) ranging from 3% to 10%
Palmitic acid ranging from 10% to 35%
Oleic acid ranging from 0.5% to 35%
Stearic acid ranging from 0.5% to 9%
Gamma-linolenic acid ranging from 0.5% to 10%
Alpha-linolenic acid ranging from 0.5% to 10%
Azelaic acid ranging from 0.5% to 20%
Linoleic acid ranging from 0.5% to 35%

Example 3

Eicosapentaenoic acid (EPA) ranging from 0.5% to 15%
Docosahexaenoic acid (DHA) ranging from 0.5% to 15%
Palmitic acid ranging from 1% to 35
Oleic acid ranging from 0.6% to 35%
Stearic acid ranging from 0.3% to 15%
Gamma-linolenic acid ranging from 0.5% to 20%
Alpha-linolenic acid ranging from 0.5% to 35%
Azelaic acid ranging from 0.5% to 35%
Linoleic acid ranging from 0.5% to 35%

Example 4

Eicosapentaenoic acid (EPA) ranging from 2% to 12%
Docosahexaenoic acid (DHA) ranging from 2% to 12%
Palmitic acid ranging from 10% to 45%
Oleic acid ranging from 1% to 35%
Stearic acid ranging from 0.5% to 25%
Gamma-linolenic acid ranging from 0.5% to 10%
Alpha-linolenic acid ranging from 0.5% to 30%
Azelaic acid ranging from 0.5% to 20%
Linoleic acid ranging from 3% to 35%

Example 5

Eicosapentaenoic acid (EPA) ranging from 35% to 24%
Docosahexaenoic acid (DHA) ranging from 3% to 24%
Palmitic acid ranging from 10% to 40%
Oleic acid ranging from 15% to 35%
Stearic acid ranging from 0.5% to 40%
Gamma-linolenic acid ranging from 0.5% to 25%
Alpha-linolenic acid ranging from 0.5% to 20%
Azelaic acid ranging from 0.5% to 25%
Linoleic acid ranging from 0.5% to 35%

Example 6

Eicosapentaenoic acid (EPA) ranging from 1% to 20%
Docosahexaenoic acid (DHA) ranging from 3% to 12%
Palmitic acid ranging from 1% to 30%
Oleic acid ranging from 2% to 15%
Stearic acid ranging from 0.5% to 15%
Gamma-linolenic acid ranging from 0.5% to 15%
Alpha-linolenic acid ranging from 0.5% to 20%
Azelaic acid ranging from 0.5% to 10%
Linoleic acid ranging from 5% to 35%

Example 7

Eicosapentaenoic acid (EPA) ranging from 0.5% to 12%
Docosahexaenoic acid (DHA) ranging from 0.5% to 12%
Palmitic acid ranging from 0.5% to 45%
Oleic acid ranging from 10% to 35%
Stearic acid ranging from 0.5% to 10%
Gamma-linolenic acid ranging from 0.5% to 20%
Alpha-linolenic acid ranging from 0.5% to 20%
Azelaic acid ranging from 0.5% to 10%
Linoleic acid ranging from 0.5% to 15%

Example 8

Eicosapentaenoic acid (EPA) ranging from 1% to 12%
Docosahexaenoic acid (DHA) ranging from 1% to 12%
Palmitic acid ranging from 0.5% to 25%
Oleic acid ranging from 10% to 35%
Stearic acid ranging from 0.5% to 10%
Gamma-linolenic acid ranging from 0.5% to 15%
Alpha-linolenic acid ranging from 0.5% to 15%
Azelaic acid ranging from 0.5% to 10%
Linoleic acid ranging from 2% to 35%

Example 9

| | |
|---|---|
| Palmitic acid | 14% |
| Linoleic acid | 12% |
| Oleic acid | 15% |

-continued

| | |
|---|---|
| Stearic acid | 14% |
| Alpha-linolenic acid | 15% |
| Gamma-linolenic acid | 0.5% |
| Azelaic acid | 0.5% |
| Eicosapentaenoic acid (EPA) | 14% |
| Docosahexaenoic acid (DHA) | 15% |

Example 10

| | |
|---|---|
| Palmitic acid | 20% |
| Linoleic acid | 10% |
| Oleic acid | 15% |
| Stearic acid | 7% |
| Alpha-linolenic acid | 10% |
| N-2-hydroxyethyl palmitamide (PEA) | 38% |

In Vitro Anti-Inflammatory Activity Evaluation

The anti-inflammatory activity of the mixture containing nine fatty acids (see Example 9), identified as AS66 has been evaluated through two experimental tests:
1. MTT Vitality test so as to identify the highest non cytotoxic dose
2. Assessment of the ability of the mixture to reduce the release of pro-inflammatory mediators (IL-6 and IL-8) by a human macrophage cell line previously sensitized with LPS Experimental Design In vivo, the inflammatory reaction is the result of a complex process determined by the response of different cell populations in the different districts of the human body. Simplifying, we can distinguish the following stages: external aggression (bacterial or other) whether or not accompanied by a real tissue injury, release of pro-inflammatory mediators, recall of competent cells, production of antibodies, antigen elimination, activation of the process of repair and healing.

Monocytes and macrophages are critical players in both natural and acquired immune responses. Macrophages exist in virtually every tissue in the body, and show striking morphological heterogeneity in different tissues. Monocytes are the blood-borne precursors of macrophages.

In the event of infection, tissue damage or other injury, large number of monocytes are recruited from the bloodstream into the site of the insult and differentiate into the appropriate macrophages phenotype (see FIG. 2).

Macrophages are also important modulators of a variety of immune responses, via secretion of a large array of cytokines and chemokines. Among the mediators produced by monocytes/macrophages, in this study were chosen one cytokine (Interleukin 6) and one chemokine (Interleukin 8).

Interleukin 8 (IL-8) has been chosen for its key role in the primary inflammatory response. It is produced constitutively by different cell populations (monocytes/macrophages, T lymphocytes, endothelial cells, neutrophils, keratinocytes, fibroblasts, and chondrocytes), and this gives it an important role in the operations of "surveillance" and "emergency" in the tissues.

Interleukin 6 (IL-6) was chosen because it is typical of the late phase of the inflammatory reaction.

The IL-6 is a glycoprotein of 26 kDa not constitutively produced, it is synthesized in response to other pro-inflammatory mediators namely "precocious" such as IL-8, IL-1α and TNF, also called primary cytokines of the inflammatory response.

The IL-6 has a role in both innate (non-specific) and in the humoral (specific) immune reaction. In innate immunity, it stimulates the production of acute phase proteins by the liver cells, which are responsible for the appearance of symptoms of systemic allergic reaction, and stimulates the maturation of neutrophils from immature precursors in the bone marrow. In the specific humoral response, it stimulates the proliferation of clones of B lymphocytes that produce antibodies specific for the allergen which triggered the reaction.

Cellular Model

Given the central role of monocytes/macrophages in cell mediated immune response and their role in the modulation of the inflammatory response in this study was selected a human cell line of monocytes called THP-1 (Human Acute monocytic leukemia). These cells have Fc, and C3b receptors, are phagocytic and grow in suspension that do not adhere to the culture flask.

The cells were purchased from the Istituto Zooprofilattico della Lombardia ed Emilia Romagna (site of Brescia—Italy) and are certified free of bacterial and mycoplasma contaminations.

Materials and Methods

The inflammatory reaction in THP-1 cells was induced by exposing them to a solution of lipopolysaccharide (LPS), a known inflammatory agent extracted from E. coli a Gram-microorganism, at a concentration of 1 ug/ml for two hours.

Culture medium: RPMI 1640, supplemented with glutamine 2 mM, 10% of Scomplemented Fetal Calf Serum, non essential amino acids, 2-Mercaptoethanol (0.05 mM) and a antibiotics mix Penicillin 2000 UI/ml. Streptomycin 1000 UI/ml, Fungizone 2 ug/ml (Euroclone).

MTT Stock solution: 5 mg/ml in water. (Sigma Aldrich)
MTT Work Solution: 1 mg/ml in RPMI 1640
Coating Buffer: Phosphate Buffer Saline (PBS)
Assay buffer: PBS with Albumin from Bovine Serum (BSA) 4%
Wash Buffer: 50 mM Tris, 0.2% Tween 20
TMB Substrate solution
Stop solution: 0.18 M $H_2SO_4$ 1. Identification of the Highest Non-Cytotoxic Dose In general, the first non-cytotoxic dose choice is the dose at which the residual % of cell viability does not differ more than 15% of the viability of the negative control.

Day 1: Seeding of Cells

After verification of the vitality of cells in culture, the same were collected and centrifuged (10 minutes at 900 rpm), the pellet was then resuspended in a suitable volume of RPMI 1640 and the cells were counted with an electronic cell counter (Scepter—Millipore). Subsequently, a cell suspension was prepared at a density of 400.000 cells/ml. This suspension was distributed in 24-microwell plates at 2: 1 ml of suspension per well (400.000 cells/well). Then the plates were placed in an incubator at 37° C. and atmosphere enriched with 5% $CO_2$ until the next day (20-22 hours).

Day 2:

Sample Preparation:

1 gr of sample (mixture of Example 9) was weighed and resuspended in a volume of ethanol sufficient to obtain a final concentration of 5 mg/ml. From this stock solution was set up a series of dilutions (2×) from 2 mg/ml to 0.312 mg/ml in RPMI medium with 5% FBS.

Inoculation of the sample: after checking the state of health and density of cells seeded on day 1, from each well was collected a volume of 0.5 ml of culture medium which was later replaced with the same volume of 2× sample dilutions previously prepared. 6 different doses of the sample were inoculated: from 1 mg/ml and 5 additional twofold dilutions were arranged from the mother solution in medium with 5% FBS. The plates were then placed in an incubator at 37° C. and atmosphere enriched with 5% $CO_2$ for 20-22 hours.

Negative control consists of cells exposed only to culture medium that represent 100% of vitality.

Day 3:

after checking the state of health and density of cells exposed to the sample, the MTT vitality test was performed MTT Vitality Test MTT is a tetrazolium salt which, in its oxidised form, is soluble and yellow in colour. It is converted into its reduced formazan salt form by cytoplasmic and mitochrondial dehydrogenases (succinate dehydrogenases), in this form the salt is insoluble and precipitates to form purplish blue crystals. The addition of isopropanol solubilises the crystals, forming a violet solution whose strength, evaluated with a 540 nm±30 spectrophotometer reading, is proportional to the quantity of live cells present at the time the test is performed.

The inoculum was removed and replaced with the same volume of the MTT working solution.

The plates were placed in an incubator for three hours. At the end of the incubation period the salt has been removed and replaced with the same volume of isopropanol. Then, after 5 minutes of shaking, the optical density was read at 570 nm (±30 nm) with a spectrophotometer (Victor X5-Perkin-Elmer)

From the analysis of the results obtained 0.1, 0.06 and 0.03 mg/ml sample concentrations were selected for the anti inflammatory test.

2. Evaluation of Anti-Inflammatory Activity

Day 1: Seeding of Cells

After verification of the vitality of cells in culture, the same were collected and centrifuged (10 minutes at 900 rpm), the pellet was then resuspended in a suitable volume of RPMI 1640 and the cells were counted with an electronic cell counter (Scepter—Millipore). Subsequently, a cell suspension was prepared at a density of 400.000 cells/ml. This suspension was distributed in Petri dishes plates: 3 ml of cell suspension/ml (1.200.000 cells/dish). Then the plates were placed in an incubator at 37° C. and atmosphere enriched with 5% $CO_2$ until the next day (20-22 hours)

Day 2:

Sample Preparation:

1 gr of powder (mixture of Example 9) was weighed and resuspended in a volume of ethanol sufficient to obtain a final concentration of 5 mg/ml. From this stock solution were set up three dilutions (2×): 0.2, 0.12 and 0.06 mg/ml in RPMI medium with 5% FBS.

Quality Control (QC):

The QC was represented by a solution of Locoidon 0.1% at 1 mg/ml, a known anti-inflammatory product containing cortisol. The solution was prepared in RPMI 1640 medium with 5% FBS.

Positive Control

The positive control was represented by cells exposed to the solution of LPS 1 g/ml Induction of the Inflammatory Reaction:

after a night of the culture the dishes were removed and about half of the culture medium was replaced with the same volume of the solution of LPS 2 µg/ml (final concentration 1 µg/ml). The exposure to LPS was continued for two hours.

Inoculation of the Sample:

At the end of the incubation time with LPS, after checking the state of health of the cells, the LPS solution was replaced with the same volume of the different doses of the sample previously prepared. The plates were then placed in an incubator at 37° C. and atmosphere enriched with 5% $CO_2$ for 20-22 hours.

Day 3 after checking the state of health of cells treated, the cell suspension was collected in 1.5 ml tubes and centrifuged (1000 g for 10 minutes). Then the ELISA test was carried out in order to evaluate the IL-6 and IL-8 concentrations in the culture medium.

Finally, in order to exclude false positives, i.e. to avoid classifying as anti-inflammatory effect the lack of living and vital cells, after centrifugation, the cells were subjected to the test of cell viability MTT.

Results

Percentage of Cell Survival

% of Vitality=$[(OD_{sample}/OD_{Neg.Control})\times 100]$

% Inhibition of Vitality=(100−% Vitality)

O.D.: optical density $O.D._{sample}$: optical density obtained from cells exposed to the sample $O.D._{Negative\ Control}$: optical density obtained from cells exposed only to the culture medium (100% Vitality)

Assessment of levels of IL-6 and IL-8 secreted in the culture medium

Anti Inflammatory Effectiveness

IL-8% Inhibition=(100−(pg/ml IL-8$_{sample}$/pg/ml IL-8$_{pos\ cntrl}$)*100)

pg/ml IL-8$_{sample}$: pg/ml of IL-8 secreted by cells exposed to the solution of LPS and then to various dilutions of sample pg/ml IL-8$_{pos\ cntrl}$: pg/ml of IL-8 secreted by cells exposed only to the solution of LPS. IL-6% Inhibition=(100−(pg/ml IL-6$_{sample}$/pg/ml IL-6$_{pos\ cntrl}$)*100)

pg/ml IL-6$_{sample}$: pg/ml of IL-6 secreted by cells exposed to the solution of LPS and then to various dilutions of sample pg/ml IL-6$_{pos.cntrl}$: pg/ml of IL-8 secreted by cells exposed only to the solution of LPS.

Acceptance Criteria of the Test

The test meets the acceptance criteria of the method if the equation of the regression line of the standard curve has a coefficient of determination (R2)≥0.8 (between 0.8 and 1).

Figure 3:
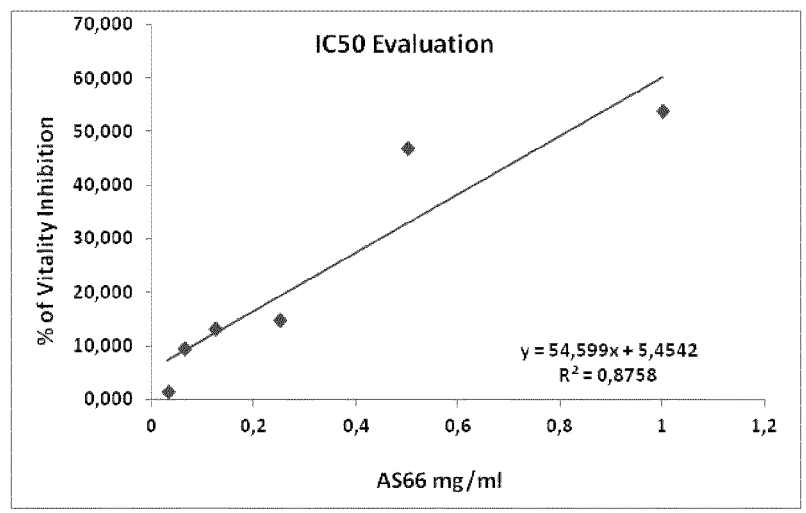
FIG. 3: Determination of $IC_{50}$ for AS66

The coefficient of variation of the raw data must be <20% p Value (T test): <0.05 a) $IC_{50}$ $IC_{50}$=0.8 mg/ml (see FIG. 3)

TABLE 1

| | Camp.AS66 | |
|---|---|---|
| mg/ml | % Vitality | % Vitality Inhibition |
| 1 | 45.97 | 54.03 |
| 0.5 | 53.05 | 46.95 |
| 0.25 | 85.19 | 14.81 |
| 0.125 | 86.66 | 13.34 |
| 0.0625 | 90.38 | 9.62 |

TABLE 1-continued

Camp.AS66

| mg/ml | % Vitality | % Vitality Inhibition |
|---|---|---|
| 0.03125 | 98.53 | 1.47 |
| 0.015625 | 95.05 | 4.95 |
| cntrl neg | 100.00 | 0.00 |

$IC_{50}$ corresponds to the dose of the sample which kills 50% of the cells in the incubation period.

b) IL-8

TABLE 2

Standard Curve IL8

| Pg/ml | OD.$_{AV}$ |
|---|---|
| 1000 | 1.230 |
| 500 | 0.821 |
| 250 | 0.471 |
| 125 | 0.252 |
| 62.5 | 0.125 |
| 31.25 | 0.0645 |
| 15.625 | 0.0175 |
| 0 | 0 |

Figure 4:
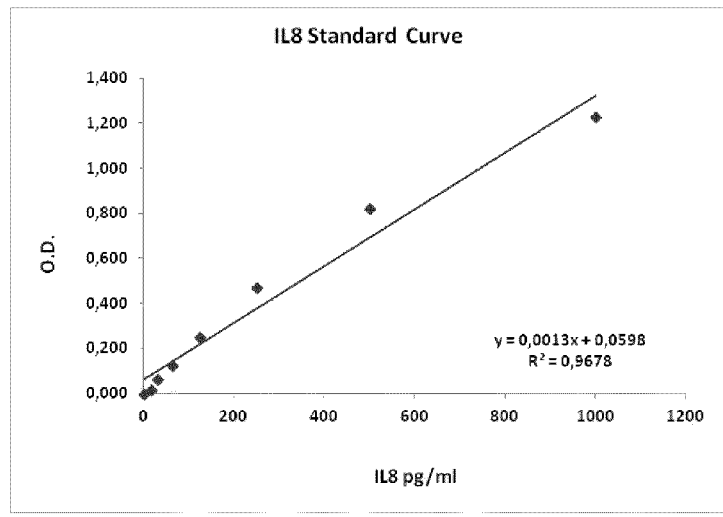
FIG. 4: Standard curve and percentage of inhibition of IL-8 with AS66
Figure 4:
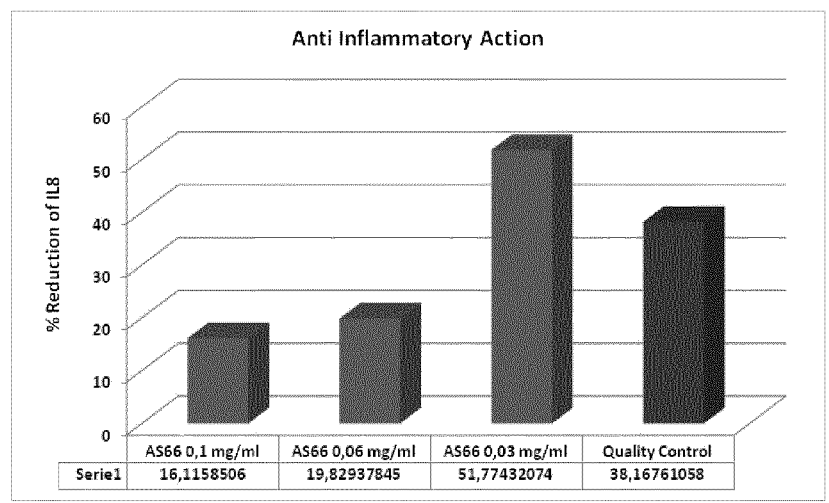

The standard curve of IL-8 and the percentage of inhibition of IL-8 are represented in FIG. 4.

TABLE 3

| AS66 + LPS | pg/ml IL8 | % Inhib. IL8 |
|---|---|---|
| AS66 0.1 mg/ml | 900.0769 | 16.116 |
| AS66 0.06 mg/ml | 860.2308 | 19.829 |
| AS66 0.03 mg/ml | 517.4615 | 51.774 |
| Neg. Control | 0 | 0 |
| Pos. Control | 1073 | 0 |
| Quality Control | 663.4615 | 38.168 | c) IL-6

TABLE 4

Standard Curve IL6

| pg/ml | OD.$_{Av}$ |
|---|---|
| 1000 | 2.196 |
| 500 | 1.751 |
| 250 | 1.140 |
| 125 | 0.6805 |
| 62.5 | 0.3265 |
| 31.25 | 0.233 |
| 15.625 | 0.0925 |
| 0 | 0 |

Figure 5:
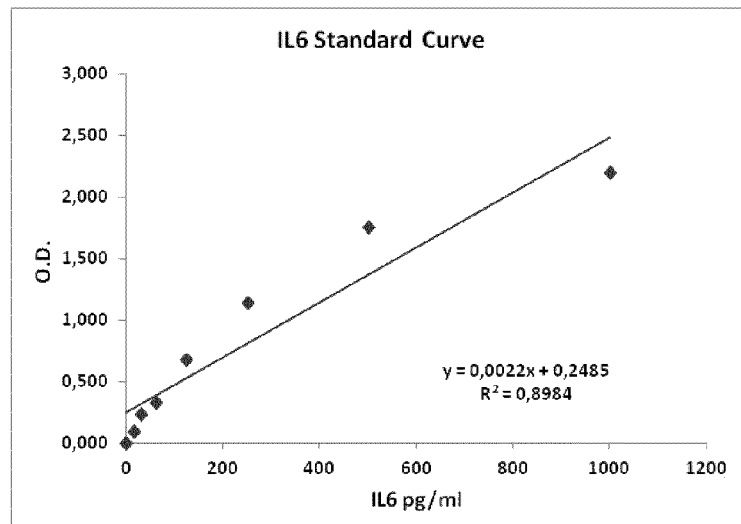
FIG. 5: Standard curve and percentage of inhibition of IL-6 with AS66
Figure 5:
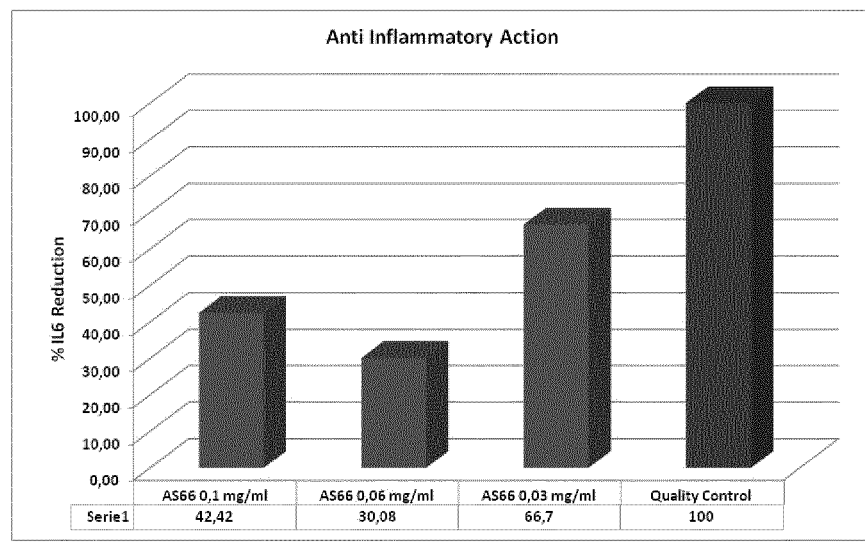

The standard curve of IL-6 and the percentage of inhibition of IL-6 are represented in FIG. 5.

TABLE 5

| AS66 + LPS | pg/ml IL6 | % Inhib. IL6 |
|---|---|---|
| AS66 0.1 mg/ml | 270.5909 | 42.422 |
| AS66 0.06 mg/ml | 328.5909 | 30.080 |
| AS66 0.03 mg/ml | 156.5 | 66.699 |
| Neg. Control | 0 | 100 |
| Pos. Control | 469.9545 | 0 |
| Quality Control | 0 | 100.000 |

As it can be appreciated, none of the doses tested showed cytotoxic action likely to distort the outcome of the evaluation of anti-inflammatory activity of the tested sample AS66 (mixture of Example 9).

All doses of AS66 analyzed have proved to be able to inhibit the release of both cytokines analyzed.

The tests performed have identified a maximum effective dose equivalent to 0.03 mg/ml: at this concentration, the anti-inflammatory activity of AS66 determines an inhibition of release of IL-6 and IL-8 equal to 51% and 66.7% respectively.

In other words, minor concentrations of the mixture according to the present invention lead to higher anti-inflammatory activity, in absence of cytotoxic effects.

The same two experimental tests were performed also on a composition comprising a mixture of five fatty acids and N-2-hydroxyethyl palmitamide (PEA) (see Example 10), identified as LC88.

Figure 6:
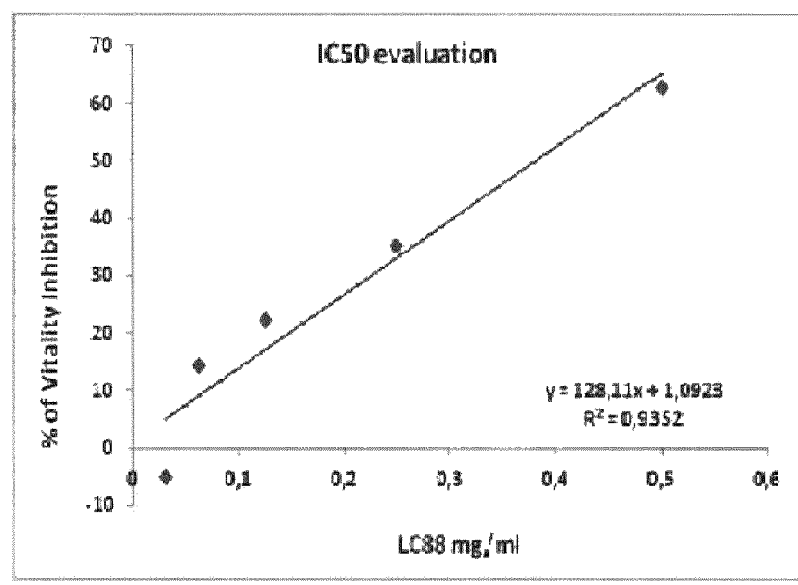
FIG. 6: Determination of $IC_{50}$ for LC88

As in the previous test. $IC_{50}$ has been identified and is of 0.38 mg/ml (see FIG. 6).

Figure 7:
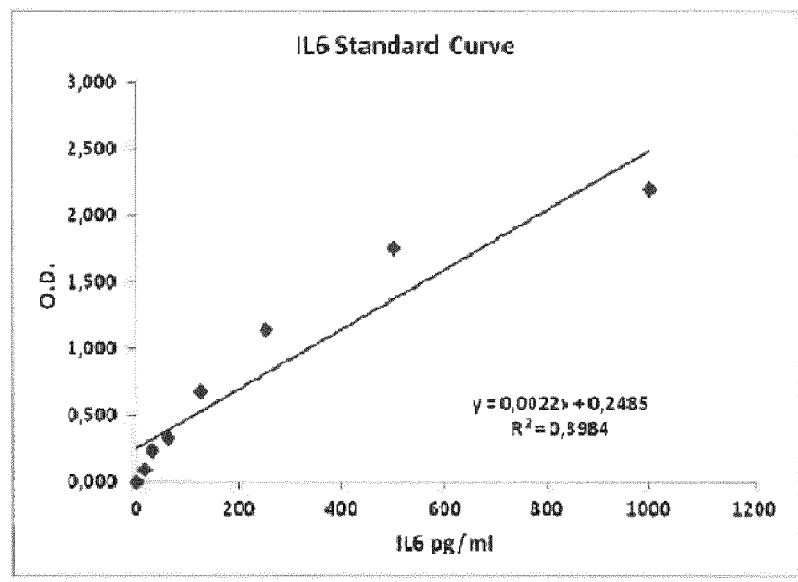
FIG. 7: Standard curve and percentage of inhibition of IL-6 with LC88
Figure 7:
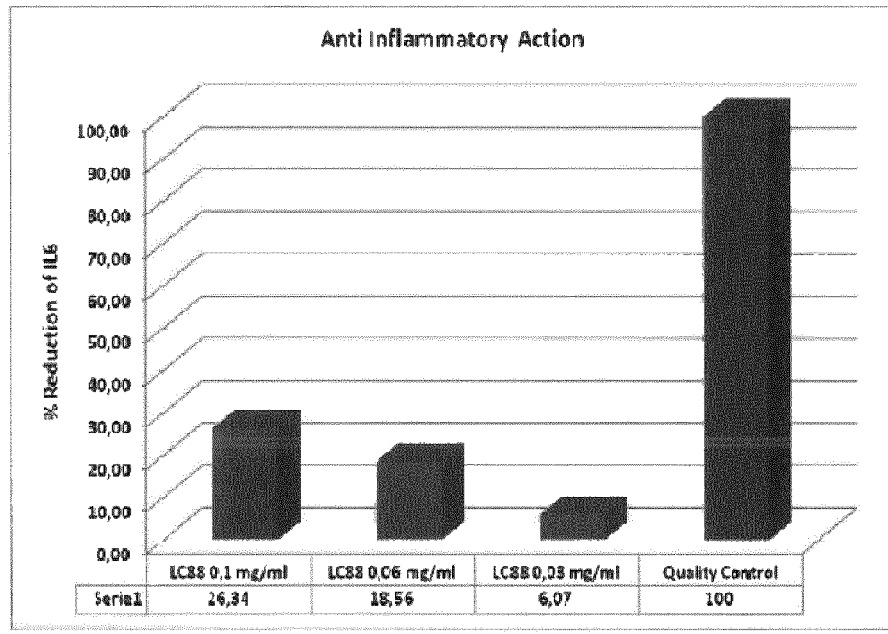

The data obtained regarding the percentage of inhibition of IL-6 are reported in the table below and in FIG. 7.

TABLE 6

| LC88 + LPS | pg/ml IL8 | % Inhib. IL8 |
|---|---|---|
| LC88 0.1 mg/ml | 374.95 | 26.342 |
| LC88 0.06 mg/ml | 414.59 | 18.555 |
| LC88 0.03 mg/ml | 478.14 | 6.072 |
| Neg. Control | 0 | 0 |
| Pos. Control | 509.05 | 0 |
| Quality Control | 0 | 100 |

As it can be easily appreciated from the above data, none of the doses showed cytotoxic action likely to distort the outcome of the evaluation of anti-inflammatory activity of the tested sample.

All doses of LC88 have proved to be able to inhibit the release of IL-6 with a significant effect dose/response.

In Vivo Testing

1. In Vivo Animal Testing

Several studies have been performed on animals in order to confirm the efficacy and safety of the mixture of the present invention (see Example 9), in particular for the control of the symptomatology in the external ears of pets (cats, dogs).

From April 2013 to October 2013 had been enrolled 33 exemplary both of cats and dogs belonging to different breeds, with many different pathologies in the external auditory canal. In particular 23 dogs and 10 cats have been observed.

Related to dogs: 5 Mastiff, 8 hunting dogs, 10 terriers.

Related to cats have been observed 10 cats, of which 8 of European breed and 2 Siamese breed, cohabiting in two colonies.

All dogs have been divided based on the etiopathogenesis/pathology and to the belonging to the breeds and classification of FCI (International Cynologic Federation).

Study 1: Clinical Study on Dogs Belonging to Class 2: Mastiff of Many Breeds Suffering of *Malassezia* (*Pityrosporum*)

5 dogs Mastiff, aged between 8 months and 5 years, three males and two females

At the first visit the external auditory canal was edematous and erythematous in both ears, with presence of earwax material and bad odor. The ear cytology discloses the presence of *Malassezia* in a very large number for each sample. The therapy provides the use of a veterinary ear disinfectant based of clorexidine to be administered twice daily, morning and evening, for 15 days. At the second visit, i.e. ten days after, we added the administration of ear drops based on fatty acids because the overgrowing yeasts had been controlled, but the auditory canal was still erythematous with persistent symptoms in the animal. After the administration of ear drops based on the mixture of Example 9, the next control after 4 days showed that the external auditory canal was normalized without erythema and without any symptoms showed by the animals.

Conclusions:

in the normal practice, at least the 40% of dogs should have had an exacerbation of the yeasts (*Pityrosporum Ovale* or *Malassezia*), in the other 40% the tissue normalization would have taken at least 15/30 days, in the remaining 20% the healing and the tissue normalization would have occurred in a period of 30/45 days. The ear drops based of the mixture of Example 9 allowed the total remission of the inflammation and the healing in a period of time of only 3/4 days in all the exemplary treated. It is very important to underline the control of inflammation in the tissues, because this approach avoid the stimulus to scratch avoiding in this way the exacerbation of the pathology and allowing a very fast healing.

Study 2: Clinical Cases on Dogs Belonging to the Class 7 (Hunting Dogs): Etiopathogenesis Foreign Body:

It has been considered 8 dogs, 5 Setter, 3 Pointer, aged between 2 and 5 years, 5 males and 3 females, carried to the veterinary clinic for a problem to one ear.

In the external auditory canal was highlighted the presence of a foreign body. After having removed said foreign body and having ascertained the integrity of the tympanic membrane, after the cleaning of the auditory meatus, it has been administered an ear product based on the mixture of Example 9 for 5 days twice daily in the morning and evening in the affected ear. After 5 days of treatment the control visit showed the complete normalization of the tissues and the disappearance of the erythema.

Conclusions:

in the normal practice 30% of animals would have developed an over infection and would have been treated with antibiotics, 40% would have had a persistent inflammation for at least 20/30 days after the removing of the foreign body and a healing in a time between 30 to 40 days, in the other 30% of animals a nearly normalization in 20 days. With the use of ear drops based of fatty acids in the post surgical phase (foreign body removal), the inflammation has been controlled allowing the complete normalization of the tissues in 4/5 days avoiding the onset of an over infection.

Study 3: Clinical Cases on Dogs Belonging to Class 3, Terrier, Etiopathogenesis Atopic Dermatitis, Allergies and Hormonal Alterations.

10 dogs, 5 west Highlands White Terrier, 3 Jack Russel Terrier, 2 Yorkshire Terrier have been observed, aged between 1 and 10 years, 7 females and 3 males.

All animals were affected by allergic dermatitis, atopic dermatitis with symptomatic otitis. Some dogs (5) at the visit showed a presence of exudate with skin scales in the external auricle. They have been administered the mixture of Example 9 as unique therapeutic device. The results were stunning; in just 3 days the situation was significantly improved until having a nearly normal skin, that allowed the possibility to perform a depth examination with otoscope.

Conclusions:

the otitis due to allergic dermatitis are quite common in 15% of the dogs population. The unique use of the mixture of the present invention allowed the resolution of the pathology, with the tissues normalization in very short time jut 3/4 days.

Study 4: Clinical Cases on European and Siamese Cats: Etiopathogenesis Ear Infections by Parasites 10 cats, 8 European and 2 Siamese, 7 females and 3 males neutered, aged between 6 months and 5 years, carried to the visit for an otitis that showed the parasitic nature. All cats showed abundant material in both ear canals with presence of mites and severe itching and 3 of them developed oto hematoma. To the therapy with Salamectina spot-on, had been added a product based of fatty acid for the tissue normalizing that determined an optimal resolution in just 2/3 days.

Conclusions:

in 70% of animals in the same pathological conditions the edema and itch would have been persisting for many days until 20/30 days, determining in this way the further damage of the tissues already inflamed. The administration of the mixture according to Example 9 allowed a tissue normalization in very short time, both normalizing the erythematous and inflammation process, and eliminating the itching sensation.

Studies Conclusion:

We observed a very fast resolution of the pathologies until the disappearance of the symptomatology in very short time. The mixture of the present invention is thus to be considered a valid therapeutic instrument for the control and the progression of inflammatory processes of variegated etiologies of pathologies affecting the external ear of pets.

These results have been confirmed by a further clinical study of a periophtalmic cream based on the mixture of Example 9 for treating pets with periophtalmic pathologies, all the exemplary that took part to the study and related pathologies are reported in the table below.

TABLE 7

| Exemplary | m/f | Age | Pathology |
|---|---|---|---|
| 2 Persiano | m/f | 18 m/3 a | allergic conjunctivitis |
| 1 Ragdoll | m | 5 a | blepharitis |
| 2 Burmese | f/f | 2 a/7 a | conjunctivitis |
| 1 Scottish Fold | m | 10 a | Conjunctivitis post septic |
| 1 Balinese | f | 2 a | blepharitis |
| 1 American Wirehair | f | 4 a | Calazio post surgical |
| 3 Bulldog | m/m/f | 15 m/3 a/5 a | Ectropion |
| 2 Yorkshire Terrier | f/f | 5 a/12 a | keratoconjunctivitis |
| 1 Shih Tzu | m | 4 a | Ectropion |
| 1 Mastiff | m | 5 a | conjunctivitis |
| 1 San Bernardo | f | 20 m | conjunctivitis |
| 2 Shar Pei | f/f | 15 m/20 m | Post-surgical inflammation |
| 2 Carlino | m/m | 1 a/5 a | keratoconjunctivitis |

All cats and dogs received a treatment with an ophthalmic cream based on the mixture of the present invention, the symptomatology status resolved in an average time of 5 days (from 3 to 9 days) with average application of twice per day.

The periophthalmic cream based on 9 fatty acids, demonstrated to be efficient in the control and in the progression of the symptomatology related to inflammation of variegated nature in the eyelids of cats and dogs.

2. In Vivo Human Testing

The following data relate to a comparative study of GutLife and EvaLife vaginal cream, both containing the mixture of the present invention and PEA, for administering to patients receiving chemo radiation for SCC anus/anal canal. This study has been performed at Southampton oncology centre.

Until recently there has been a limited amount of products available for this patient group to use for any skin reaction that develops while undergoing radiotherapy.

GutLife and EvaLife (pH balanced for females) are creams that contain the mixture of the present invention (see Example 10) and that can be used for the treatment of skin/mucosal changes (itching, burning, redness, swelling and tenderness) in the anal and peri-anal area in patients undergoing radiation or chemotherapy.

GutLife is an anal and peri-anal cream that both male and female patients can use. EvaLife is specifically for female patients to use around vagina and vulva, it is pH balanced to be more beneficial for female patients.

Study

It is proposed that we trial GutLife and EvaLife to assess its benefit to the patient and if it reduces hospital admissions for this group of patients. The study makes use of the RTOG scale for skin assessment as advised by the Society of Radiographers and used in Southampton Oncology Centre. The clinician and/or colorectal radiographer assessed and recorded this weekly. The RTOG and pain scores were used for four patients (two male and two female) as a control group compared to a $2^{nd}$ group that used GutLife and EvaLife products. Assessments were made in the same weekly review clinic each week during the patient's course of treatment. Results can be summarized and collected in a table Dose Prescription Phase I: 30.6 Gy to MPD (ICRU reference point) in 17 fractions Phase II: 19.8 Gy to 100% for conformal plan (ICRU reference point) in 11 daily fractions.

Max dose 107%, minimum 95% within PTV (Planning Target Volume).

OR: 19.8 Gy to MPD in 11 daily fractions if parallel opposed fields

Concurrent Chemotherapy

Patients have received concurrent chemotherapy via a PICC (peripherally inserted central catheter) line as an outpatient.

Mitomycin C 12 mg/m² IV bolus Say 1 (max 20 mg)

5-Fluorouracil 1000 mg/m²/day continuous infusion days 1-4 (week 1) and day 29-32 (week 5).

The chemotherapy was delivered prior to receiving first fraction of radiotherapy The RTOG skin assessment tool was used as advised by the Society of Radiographers in order to evaluate the skin reaction (see table 8)

TABLE 8

| RTOG 0 | RTOG 1 | RTOG 2A | RTOG 2B | RTOG 3 |
|---|---|---|---|---|
| No visible change to skin | Faint or dull erythema | Tender or bright erythema | Patchy moist desquamation moist oedema | Confluent moist desquamation |

Patients underwent radical radiotherapy treatment for SCC anus/anal canal with concurrent chemotherapy April 2012-April 2013 at Southampton Oncology Centre. 28 female patients and 11 male patients were treated in this period.

From data gathered over the past 12 months there were 39 patients treated during this time from which there were 6 confirmed admissions to the ward for adverse skin reactions attributed to radiotherapy, of this group 4 were female patients and 2 male.

TABLE 9

Outcomes in anal cancer patients (control group)

| | Control Group | | | |
|---|---|---|---|---|
| | Patient A Male | Patient B Male | Patient C Female | Patient D Female |
| Maximum RTOG score Location | 3 (recorded in week 4) Scrotum, anus, perineum and groin | 3 (recorded in week 5) Scrotum, anus, perineum and groin | 3 (recorded in week 6) Peri anal and groin | 3 (recorded in week 5) Vagina, anus perineum and groin |
| Maximum pain score (1-10) | 8 | 6 | 7 | 8 |
| Aqueous Cream | Yes | Yes | Yes | Yes |
| Use of Purilon gel | No | No | Yes | Yes |
| Use of Jelonet dressings | No | Yes | Yes | Yes |
| Medication | Ibuprofen, Co-codamol + oramorph | Oramorph, Zomorph. | Paracetamol, Ibuprofen, topical morphine and oramorph | Paracetamol, Ibuprofen, topical morphine and oramorph |

TABLE 10

Outcomes in anal cancer patients (Trial group)

| | GutLife and EvaLife | | | |
|---|---|---|---|---|
| | Patient 1 Male | Patient 2 Male | Patient 3 Female | Patient 4 Female |
| Maximum RTOG score Location | 3 (recorded in week 6) Anus, groin + scrotum | 2b (recorded in week 6) Anus + scrotum | 2b (recorded in week 5) Anus, perineum + groin | 3 (recorded in week 5) Anus, perineum + groin |
| Maximum pain score (1-10) | 5 | 5 | 4 | 7 |
| GutLife/ EvaLife | GutLife | GutLife | GutLife and EvaLife | GutLife and EvaLife |
| Total n.o of GutLife/ EvaLife tubes used | 6 GutLife | 7 GutLife | 5 EvaLife 4 GutLife (9 total) | 4 EvaLife 4 GutLife (8 total) |
| Use of Purilon gel | No | No | No | Yes |
| Use of Jelonet dressings | No | No | Yes | Yes |
| Medication | Codeine + oramorph | Tramadol (arthritis) + paracetamol | Paracetamol | Paracetamol, Co-codamol, oramorph + topical morphine |

Summary

Due to the limited availability of GutLife and EvaLife, the products could only be used for four patients. Although limited in patient numbers there is still valid observations and indications from this study.

The maximum RTOG score for all patients in the control group was 3 compared to two patients scoring 3 (1 male, 1 female) using GutLife and EvaLife also the highest RTOG score for patients using GutLife/EvaLife occurs later in treatment compared to the control group. This would suggest that GutLife and EvaLife do act preventatively.

There appears to be a distinct contrast between the maximum pain scores of the control group and the GutLife/EvaLife group. The highest pain score recorded for the control group was 8 (recorded in two patients) with a lowest score of 6 (recorded in 1 patient) compared to a high score of 7 in the study group (recorded in 1 patient), the lowest pain score recorded in the trial group was 4.

One patient was admitted to hospital from the control group due to the skin reaction developed from treatment. One patient was admitted to hospital from the study group, but this was not due to a skin reaction.

From this limited study the patients who were using GutLife and EvaLife cream managed the radiotherapy induced skin reaction better than those in the control group, reporting on average a lower pain score, a lower maximum RTOG score as well as delaying the onset of the skin reaction until the last two weeks of treatment. Based on these favourable results the radiotherapy consultants for anal cancer would support a larger multicentre trial and/or include GutLife and EvaLife cream to be used for the routine skin care of anal cancer patients undergoing radiotherapy in Southampton Oncology Centre.

The invention claimed is:

1. A mixture of nine fatty acids selected from palmitic acid, oleic acid, stearic acid, linoleic acid, alpha-linolenic acid, gamma-linolenic acid, eicosapentaenoic acid (EPA), docosahexaenoic acid (DHA), azelaic acid and myristic acid, wherein the palmitic acid, if present, is contained in said mixture in a quantity between 0.2% and 48% by weight; the oleic acid, if present, is contained in said mixture in a quantity between 0.2% and 38% by weight; the stearic acid, if present, is contained in said mixture in a quantity between 0.2% and 42% by weight; the linoleic acid, if present, is contained in said mixture in a quantity between 0.2% and 40% by weight; the alpha-linoleic acid, if present, is contained in said mixture in a quantity between 0.2% and 38% by weight; the gamma-linolenic acid, if present, is contained in said mixture in a quantity between 0.2% and 30% by weight; the eicosapentaenoic acid, if present, is contained in said mixture in a quantity between 0.2% and 25% by weight; the docosahexaenoic acid, if present, is contained in said mixture in a quantity between 0.2% and 25% by weight; the azelaic acid, if present, is contained in said mixture in a quantity between 0.2% and 40% by weight; and the myristic acid, if present, is contained in said mixture in a quantity between 0.005% and 0.01% by weight, with respect to the total weight of the mixture.

2. A pharmaceutical, cosmetic, and/or dietary composition comprising a mixture according to claim 1, and at least one physiologically acceptable excipient.

3. A composition according to claim 2, characterised in that the palmitic acid is contained in said composition in a quantity between 5% and 45% by weight; the oleic acid is contained in said composition in a quantity between 2% and 35% by weight; the stearic acid is contained in said composition in a quantity between 2% and 35% by weight; the linoleic acid is contained in said composition in a quantity between 1% and 40% by weight; the alpha-linolenic acid is contained in said composition in a quantity between 1% and 25% by weight; the gamma-linolenic acid is contained in said composition in a quantity between 0.5% and 10% by weight; the eicosapentaenoic acid is contained in said composition in a quantity between 1% and 20% by weight; the docosahexaenoic acid is contained in said composition in a quantity between 1% and 25% by weight; the azelaic acid is contained in said composition in a quantity between 0.5% and 10% by weight; the myristic acid is contained in said composition in a quantity between 0.05% and 1%, with respect to the total weight of the composition.

4. A composition according to claim 2, formulated in oral, topical, rectal, vaginal, ophthalmic or parenteral form.

5. A composition according to claim 4, characterised in that said oral form is selected from the group consisting of a tablet, capsule, granule, oily capsule, solution, suspension, carrier, and nebuliser solution.

6. A composition according to claim 4, characterised in that said topical form is selected from the group consisting of a cream, ointment, gel, solution, suspension, spray, patch, and lyophilised granular powder.

7. A composition according to claim 4, characterised in that said parenteral form is an aqueous buffer solution or an oily suspension.

8. A composition according to claim 4, characterised in that said rectal form is a suppository, an enema, or a solution for endocavitary use.

9. A composition according to claim 4, characterised in that said vaginal form is a pessary, a catheter, a gel, or a solution for endocavitary use.

10. A composition according to claim 4, characterised in that said ophthalmic form is eyedrops, a wash, a cream, or an ointment.

11. A composition according to claim 2, characterised in that the mixture is present in said composition in a quantity between 10% and 60% by weight.

12. The composition according to claim 11, characterised in that the mixture is present in said composition in a quantity between 15% and 45% with respect to the total weight of the composition.

13. A composition according to claim 2, characterised in that said composition is a dermocosmetic composition, a pharmaceutical substance, a dietary supplement, or a drug.

14. The composition according to claim 2, wherein the at least one physiologically acceptable excipient is N-2-hydroxyethyl palmitamide.

15. A method of treating or preventing an inflammatory pathology in a human subject in need of therapy, comprising administering to a subject an effective amount of a pharmaceutical composition including a mixture of at least nine fatty acids selected from palmitic acid, oleic acid, stearic acid, linoleic acid, alpha-linolenic acid, gamma-linolenic acid, eicosapentaenoic acid (EPA), docosahexaenoic acid (DHA), azelaic acid and myristic acid mixture.

16. The method according to claim 15, wherein the inflammatory pathology is in the acute or chronic phase.

17. The method according to claim 15, wherein the inflammatory pathology include atopic dermatitis, dermatomyositis, scleroderma, psoriasis, polymyositis, pemphigus, or pemphigoid epidermolysis bullosa.

18. The method according to claim 15, wherein the inflammatory pathology include Sjogren's syndrome, sympathetic ophthalmia, uveitis, or uveo-retinitis.

19. The method according to claim 15, wherein the inflammatory pathology include mucosal pathologies, such as inflammation of the gastrointestinal mucous membranes (Crohn's disease) or inflammation of the oral and genital mucosa.

20. The method according to claim 15, characterised in that said inflammatory pathologies include articular and connective pathologies such as rheumatoid arthritis, psoriatic arthritis, arthritis from lupus erythematosus, or discoid or systemic lupus erythematosus.

21. The method according to claim 15, wherein the inflammatory pathology include chronic pathological inflammations, such as chronic solar dermatitis, asthma and intestinal and pulmonary fibrosis, or chronic arthritis.

22. The method according to claim 15, wherein the inflammatory pathology include degenerative pathologies affecting the PNS and the CNS, such as multiple sclerosis, autoimmune neurodegenerative pathologies, non-autoimmune neurodegenerative pathologies, inflammatory processes connected to the CNS, such as Parkinson's disease, senile dementia, bacterial meningitis, HIV infection and traumatic injuries, or a pathology of the PNS, such as radiculopathy caused by inflammation.

23. The method according to claim 15, wherein the inflammatory pathology is a pathology of the central and peripheral nervous system where the inflammatory processes follow the first ischemic insult, such as neuropathies due to compression, as well as traumatic neuropathies, cerebral strokes and cranial traumas.

24. The method according to claim 15, wherein the inflammatory pathology is a cardiological disease deriving from perfusion phenomena as a consequence of ischemic injuries.

25. The method according to claim 15, characterised in that said mixture and/or composition is administered daily, within a range of one to four doses a day.

26. The method according to claim 25, characterised in that said mixture and/or composition is administered for at least four weeks.

27. The method according to claim 25, characterised in that said dose contains from 0.1 to 50 mg of composition/kg of the patient's bodyweight.

28. The method according to claim 27, characterised in that said dose contains from 0.5 to 20 mg/kg of the patient's bodyweight.

29. A method of treating or preventing an inflammatory pathology in a animal subject in need of therapy, comprising administering to a subject an effective amount of a pharmaceutical composition including a mixture of at least nine fatty acids selected from palmitic acid, oleic acid, stearic acid, linoleic acid, alpha-linolenic acid, gamma-linolenic acid, eicosapentaenoic acid (EPA), docosahexaenoic acid (DHA), azelaic acid and myristic acid.

30. The method according to claim 29 wherein the inflammatory pathology is used for treatment of neurogenic inflammations, articular and connective pathologies such as laminitis in horses, arthritis, respiratory pathologies, ophthalmic inflammation, keratoconjunctivitis sicca, and allergic inflammatory manifestations.

31. The method according to claim 29 wherein the inflammatory pathology is administered daily, within a range of one to four doses a day.

32. The method according to claim 29 wherein the inflammatory pathology is administered for at least four consecutive weeks.

33. The method according to claim 29, wherein the inflammatory pathology wherein each of said doses contains from 0.1 to 50 mg of composition/kg of the animal's bodyweight.

34. The method according to claim 29, wherein each of said doses contains 0.5 to 20 mg/kg of the animal's bodyweight.

\* \* \* \* \*

UNITED STATES PATENT AND TRADEMARK OFFICE
CERTIFICATE OF CORRECTION

Page 1 of 1

PATENT NO. : 11,020,365 B2
APPLICATION NO. : 14/772768
DATED : June 1, 2021
INVENTOR(S) : Lodovico Burattin It is certified that error appears in the above-identified patent and that said Letters Patent is hereby corrected as shown below:

On the Title Page

ITEM (71):
Column 1, Applicant: Thiene should read as Schio.

Signed and Sealed this
Twenty-seventh Day of July, 2021

Drew Hirshfeld
*Performing the Functions and Duties of the*
*Under Secretary of Commerce for Intellectual Property and*
*Director of the United States Patent and Trademark Office*